(12) United States Patent
Stalcup et al.

(10) Patent No.: US 6,447,514 B1
(45) Date of Patent: Sep. 10, 2002

(54) POLYMER FILLED HIP FRACTURE FIXATION DEVICE

(75) Inventors: Gregory C. Stalcup, Columbia City; Antony J. Lozier, Warsaw, both of IN (US)

(73) Assignee: Zimmer, Warsaw, IN (US)

( * ) Notice: Subject to any disclaimer, the term of this patent is extended or adjusted under 35 U.S.C. 154(b) by 0 days.

(21) Appl. No.: 09/520,351

(22) Filed: Mar. 7, 2000

(51) Int. Cl.[7] .............................................. A61B 17/68
(52) U.S. Cl. ...................................... 606/63; 623/23.58
(58) Field of Search ........................ 606/63; 623/16.11, 623/23.48, 23.61, 23.62, 23.58

(56) References Cited

U.S. PATENT DOCUMENTS

| 4,274,163 | A | * | 6/1981 | Malcom et al. ............... 606/94 |
| 4,313,434 | A | | 2/1982 | Segal ........................... 128/92 |
| 4,399,814 | A | * | 8/1983 | Pratt, Jr. et al. .............. 606/94 |
| 4,576,152 | A | * | 3/1986 | Muller et al. ................. 606/93 |
| 4,625,722 | A | * | 12/1986 | Murray ........................ 606/95 |
| 4,627,434 | A | * | 12/1986 | Murray ........................ 606/63 |
| 4,662,887 | A | | 5/1987 | Turner et al. ................. 623/16 |
| 4,714,478 | A | | 12/1987 | Fischer ........................ 623/23 |
| 4,808,184 | A | * | 2/1989 | Tepic ........................... 604/56 |
| 4,815,454 | A | * | 3/1989 | Dozier, Jr. .............. 128/92 VQ |
| 4,994,065 | A | * | 2/1991 | Gibbs et al. .................. 606/92 |
| 5,102,413 | A | | 4/1992 | Poddar ........................ 606/62 |
| 5,303,718 | A | | 4/1994 | Krajicek ...................... 128/897 |
| 5,306,277 | A | * | 4/1994 | Bryant et al. ................. 606/93 |
| 5,350,379 | A | * | 9/1994 | Spievack ...................... 606/63 |
| 5,423,850 | A | | 6/1995 | Berger ......................... 606/192 |
| 5,480,400 | A | | 1/1996 | Berger ......................... 606/60 |
| 5,514,137 | A | | 5/1996 | Coutts ......................... 606/62 |
| 5,645,597 | A | * | 7/1997 | Krapiva ....................... 623/17 |
| 5,658,310 | A | * | 8/1997 | Berger ......................... 606/192 |
| 5,681,289 | A | | 10/1997 | Wilcox et al. ............... 604/175 |
| 5,693,099 | A | * | 12/1997 | Harle .......................... 623/16 |
| 5,824,087 | A | * | 10/1998 | Aspden et al. ................ 623/16 |
| 5,827,289 | A | | 10/1998 | Reiley et al. ................. 606/86 |
| 5,951,160 | A | | 9/1999 | Ronk .......................... 366/130 |
| 5,997,582 | A | | 12/1999 | Weiss .......................... 623/23 |
| 6,066,154 | A | * | 5/2000 | Reiley et al. ................. 606/192 |
| 6,132,214 | A | * | 10/2000 | Suhonen et al. ............. 433/201.1 |
| 6,228,092 | B1 | * | 5/2001 | Mikhail ....................... 606/105 |
| 6,231,615 | B1 | * | 5/2001 | Preissman ................... 623/23.73 |

* cited by examiner

Primary Examiner—Gene Mancene
Assistant Examiner—Michael B. Priddy
(74) Attorney, Agent, or Firm—Jacque R. Wilson

(57) ABSTRACT

An orthopaedic implant includes a flexible bag; a structural support at least partially within the bag; and a hardened polymer within the bag. The orthopaedic implant is implanted within the bone by forming a cavity in the bone; inserting a flexible bag into the cavity; filling the bag with a polymer; and hardening the polymer.

9 Claims, 15 Drawing Sheets under the section entitled "Background of the Invention" and shown in FIG. 1. On the other hand, orthopaedic

POLYMER FILLED HIP FRACTURE FIXATION DEVICE

BACKGROUND OF THE INVENTION

1. Field of the Invention

The present invention relates to orthopaedic implants, and, more particularly, to fracture fixation devices for femoral neck fractures.

2. Description of the Related Art

Treatment of bone fractures, voids and other defects may include the use of metal orthopaedic hardware such as implants, plates, screws, etc. In the case of a fracture in the neck region of a femur adjacent to the femoral head, a common surgical technique utilizes a compression tube and plate system (FIG. 1). The plate is attached to the lateral side of the femur and then screwed in place to the femur. A compression tube extends into an opening formed in the femur and is generally aligned with the femoral head. A screw is placed within the compression tube that is screwed into the femoral head.

SUMMARY OF THE INVENTION

The present invention provides an orthopaedic implant and corresponding implanting method utilizing a porous flexible bag, one or more structural supports within the bag and a high strength polymer within the bag.

The invention comprises, in one form thereof, an orthopaedic implant including a flexible bag; a structural support at least partially within the bag; and a hardened polymer within the bag.

The invention comprises, in another form thereof, a method of implanting an orthopaedic implant in a bone, including the steps of forming a cavity in the bone; inserting a flexible bag into the cavity; filling the bag with a polymer; and hardening the polymer.

An advantage of the present invention is that the shape of the orthopaedic implant conforms to the shape of the cavity formed in the bone.

Another advantage is that only a small incision is required to insert the various components of the orthopaedic implant into the cavity within the bone.

Yet another advantage is that compression loading of the bone may be effected.

A further advantage is that the bag may be porous to allow the polymer to pass therethrough to some extent; may be contoured to fit within a predefined cavity shape; or may be contourable to fit within a varying cavity shape.

Still another advantage is that a flexible reamer may be utilized to ream extension portions of the cavity within the bone.

Another advantage is that the polymer within the bag may be curable using thermal energy, light energy, X-ray energy, or a chemical catalyst.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Figure 1:
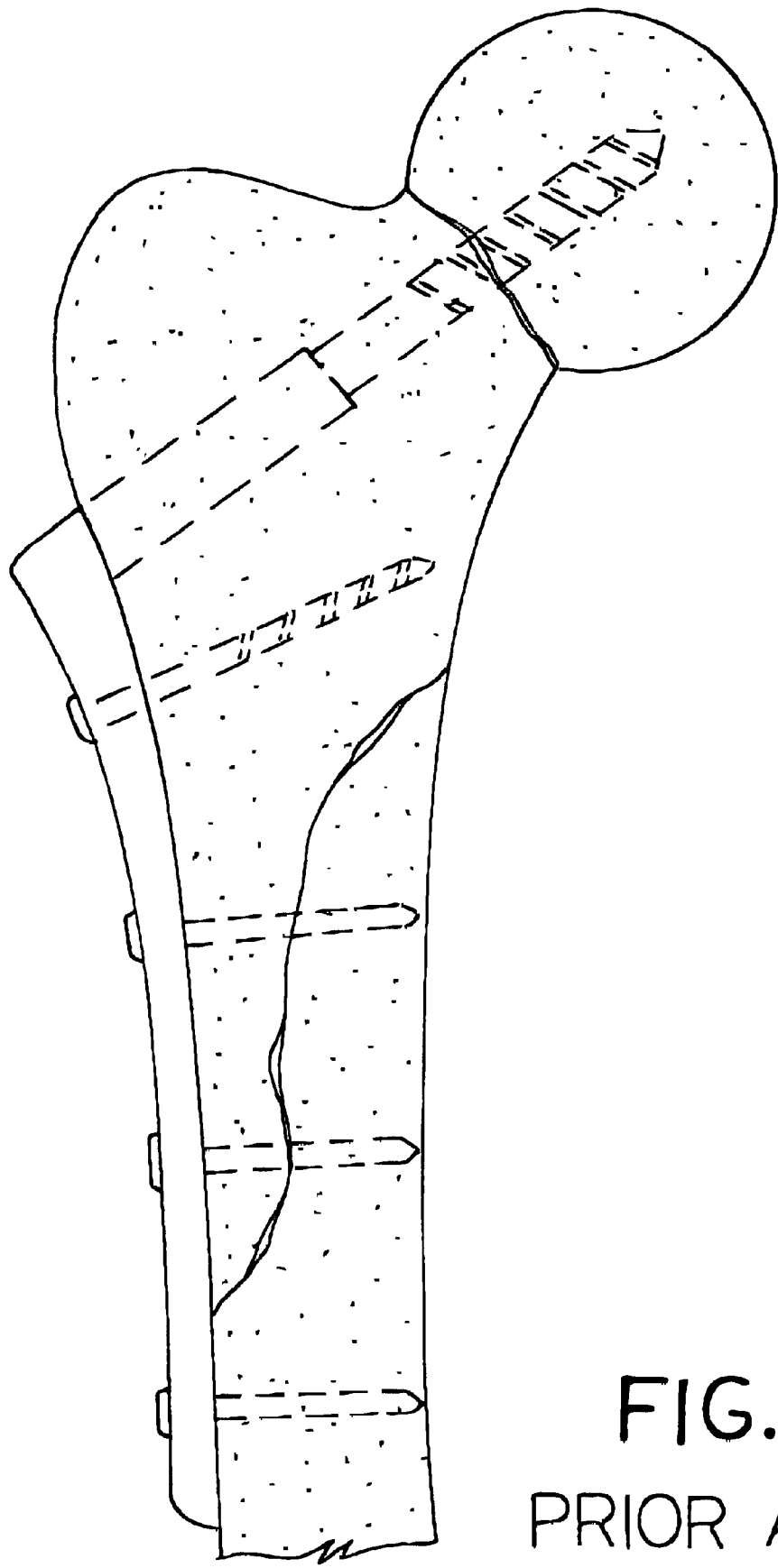
FIG. 1 is a side view of conventional orthopaedic hardware used to fixate a femoral head on a femur.
Figure 2:
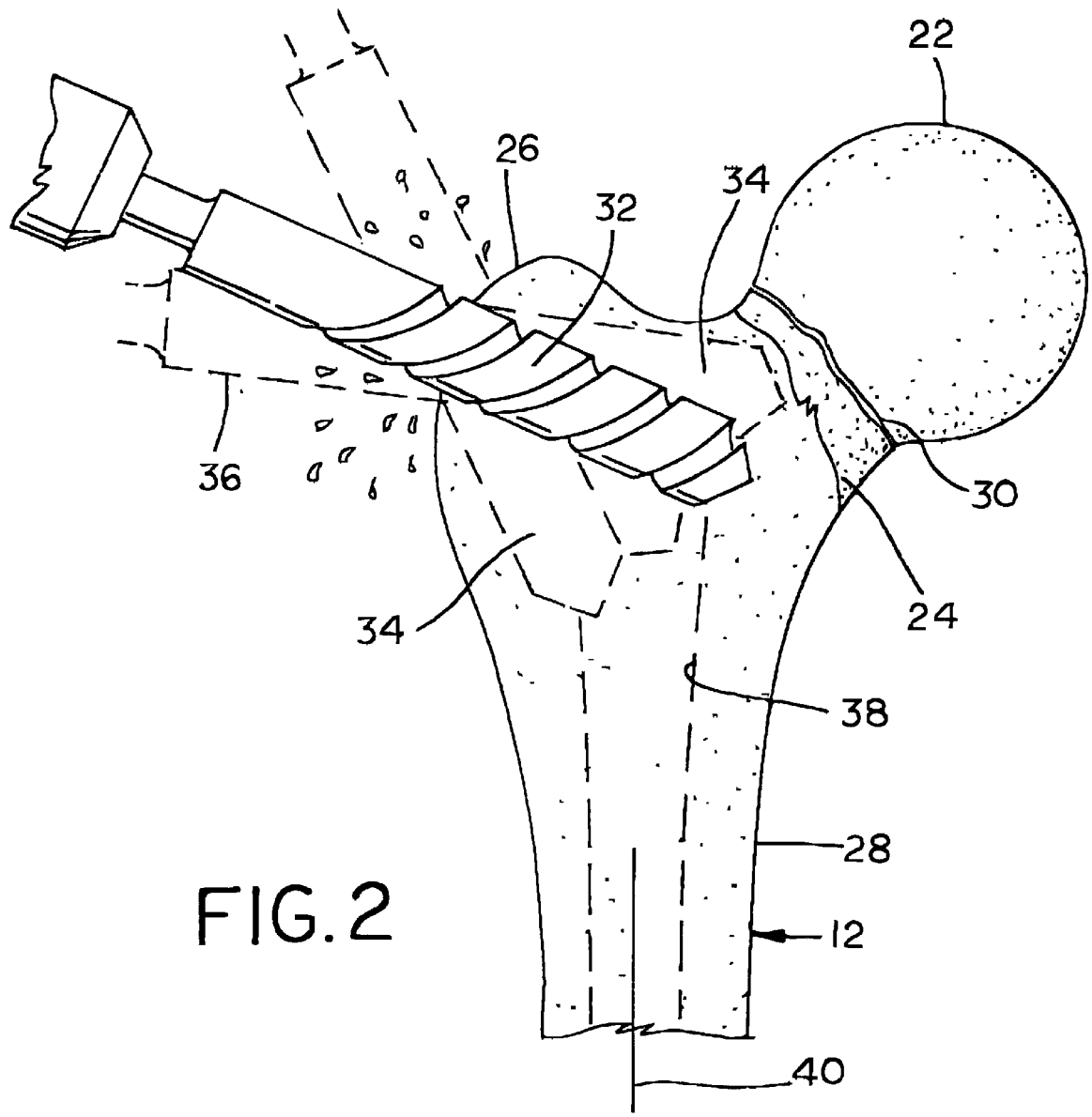
FIG. 2 illustrates the formation of a cavity within the proximal end of a femur using a drill.

Corresponding reference characters indicate corresponding parts throughout the several views. The exemplifications set out herein illustrates one preferred embodiment of the invention, in one form, and such exemplifications are not to be construed as limiting the scope of the invention in any manner.

DETAILED DESCRIPTION OF THE INVENTION

Referring now to the drawings and more particularly to FIGS. 2–12, an embodiment of the method of implanting an orthopaedic implant 10 (FIG. 10) in a bone 12 will be described in further detail. In general, orthopaedic implant 10 is in the form of a flexible bag 13 having a high strength polymer 14 which is injected under pressure therein and hardened. A plurality of structural supports, such as indicated by reference numbers 16, 18 and 20 are used to provide structural reinforcement of orthopaedic implant 10, as well as for delivery of the high strength polymer within bag 13 as will be described in greater detail hereinafter. In the method of implanting orthopaedic implant 10 described hereinafter, bone 12 is in the form of a femur. However, it is to be understood that orthopaedic implant 10 has a variety of applications and may thus be adapted accordingly.

Femur 12 is shown as including a head 22, neck 24, greater trochanter 26 and shaft 28. Head 22 is assumed to have fractured relative to neck 24, as indicated by fracture line 30. Conventionally, head 22 is fixated relative to neck 24 using a compression tube and plate system, as described above under the section entitled "Background of the Invention" and shown in FIG. 1. On the other hand, orthopaedic implant 10 of the present invention and the corresponding implantation method uses a novel bag and polymer as described hereinafter.

Preliminarily, a small incision (e.g., 18–25 mm) is cut adjacent greater trochanter 26 of femur 12. The incision location may be approximately the same as used for the placement of a gamma nail within femur 12. After forming an access hole in greater trochanter 26 using a bit 32 (FIG. 2), a flexible reamer 52 is used to form a cavity 34 in femur 12. Reamer 52 may be moved in an axial direction in and out of cavity 34 as well as being swept in the distal direction as shown to assist in the formation of fan-shaped cavity 34. Cavity 34 is generally formed to provide access to femoral head 22, as well as intramedullary (IM) canal 38 of shaft 28 defining an anatomical axis 40 of femur 12.

Figure 3:
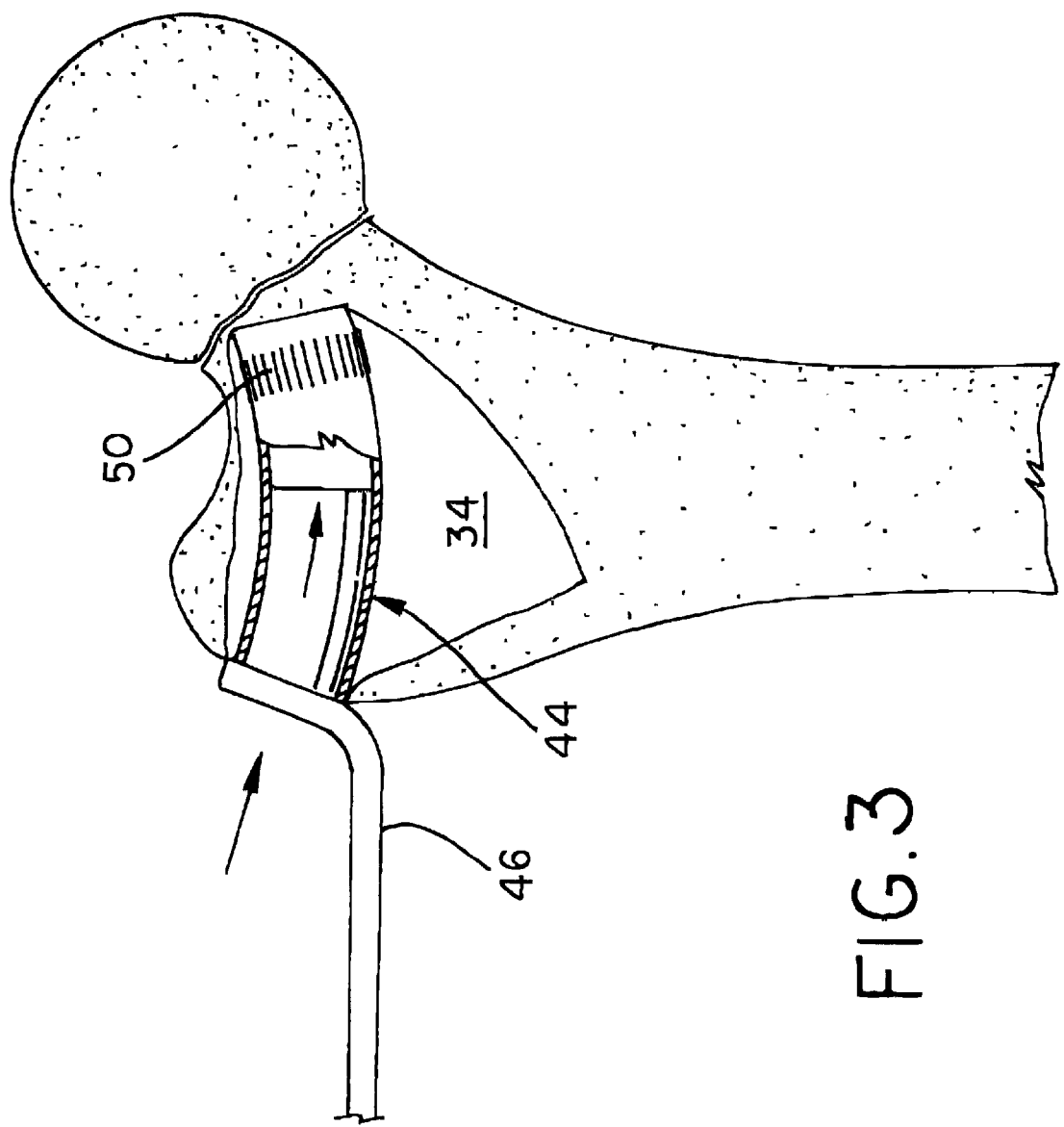
FIG. 3 illustrates a guide tube placed within the cavity.
Figure 4:
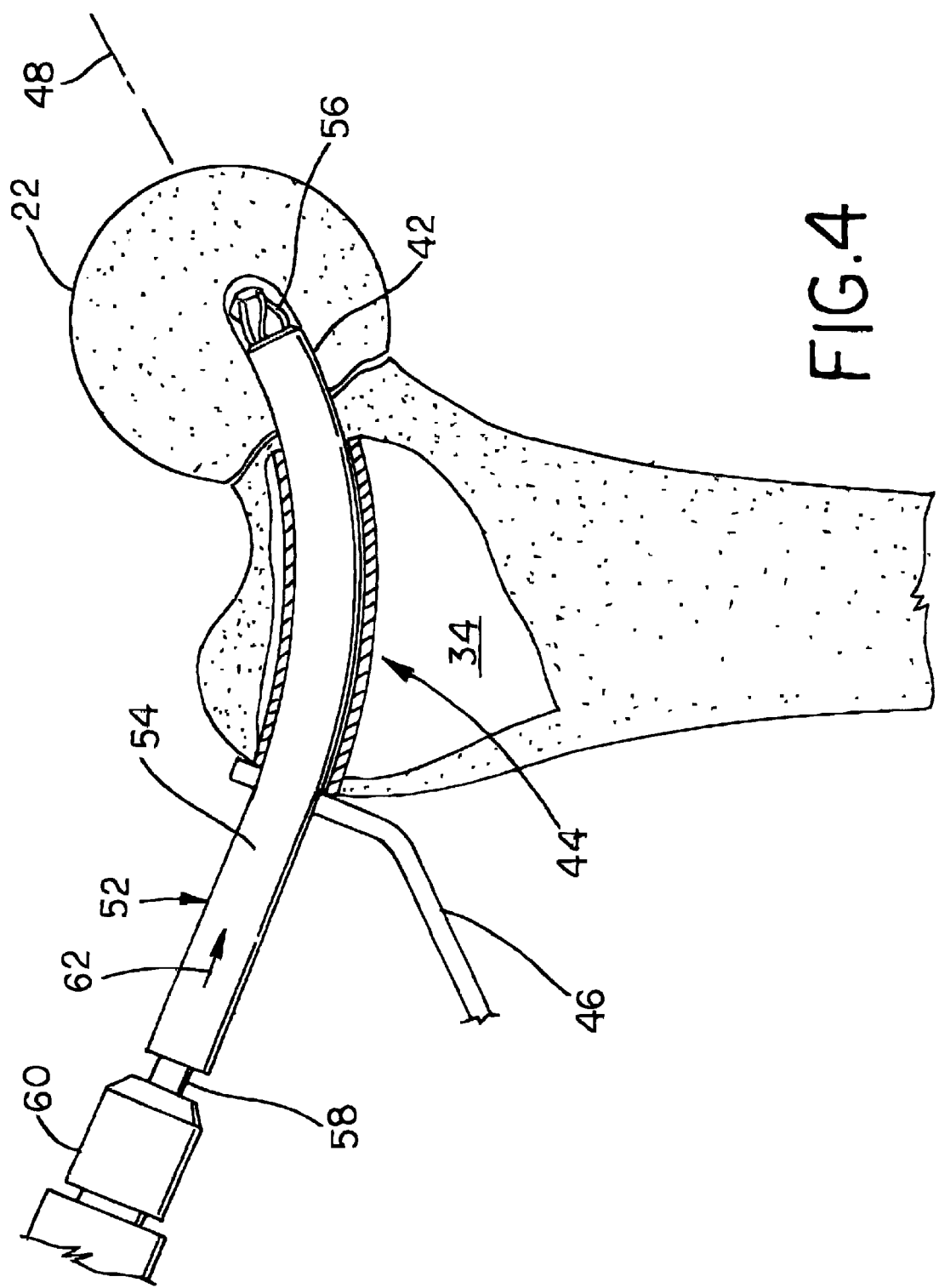
FIG. 4 illustrates a flexible reamer inserted through the guide tube of FIG. 3 to form an extension portion of the cavity extending into the femoral head.

Cavity 34 is then formed with a first extension portion 42 extending into femoral head 22 (FIGS. 3 and 4). More particularly, a guide tube 44 with an attached handle 46 is inserted within cavity 34. Guide tube 44 has a curvature allowing the formation of first extension portion 42 of cavity 34 into femoral head 22. Guide tube 44 preferably has a curvature which terminates generally parallel to a load axis 48 on femoral head 22 when engaged with an acetabular cup in the pelvic bone of the patient. Guide tube 44 may have a knurled outer surface 50 which at least under certain conditions assists gripping and placement within cavity 34. Handle 46 also assists in proper placement of guide tube 44 within cavity 34.

After guide tube 44 is positioned within cavity 34 as shown in FIGS. 3 and 4, a flexible reamer 52 is used to form first extension portion 42 within femoral head 22. Flexible reamer 52 generally includes a flexible, hollow tube 54, cutting head 56 and driven shank 58. Driven shank 58 is rotatably driven by a drive source 60, such as a hand-held rotatable drive source. Flexible tube 54 allows flexible reamer 52 to flex during extension through curved guide tube 44. Cutting head 56 at least includes axially facing cutting teeth and preferably also includes radially facing cutting teeth. Cutting head 56 forms an extension portion 42 of cavity 34 which extends into femoral head 22 approximately to the center of femoral head 22. First extension portion 42 has a diameter of between 0.25 and 0.35 inch. Upon insertion of flexible reamer 52 through curved guide tube 44, as indicated by arrow 62, cutting head 56 impinges against femur 12 adjacent the end of curved guide tube 44, at which point some resistance is felt by the surgeon. The position of flexible, hollow tube 54 relative to handle 46 may be observed by the surgeon, after which flexible reamer 52 is moved in an axial direction into curved guide tube 44 a predetermined amount which causes first extension portion 42 to extend generally to the center of femoral head 22. Flexible, hollow tube 54 may optionally be provided with visual indicia at incremented placement locations along its length to assist in the formation of first extension portion 42 in femoral head 22. After first extension portion 42 is formed in femoral head 22, flexible reamer 52 and curved guide tube 44 are each removed from within cavity 34.

Figure 5:
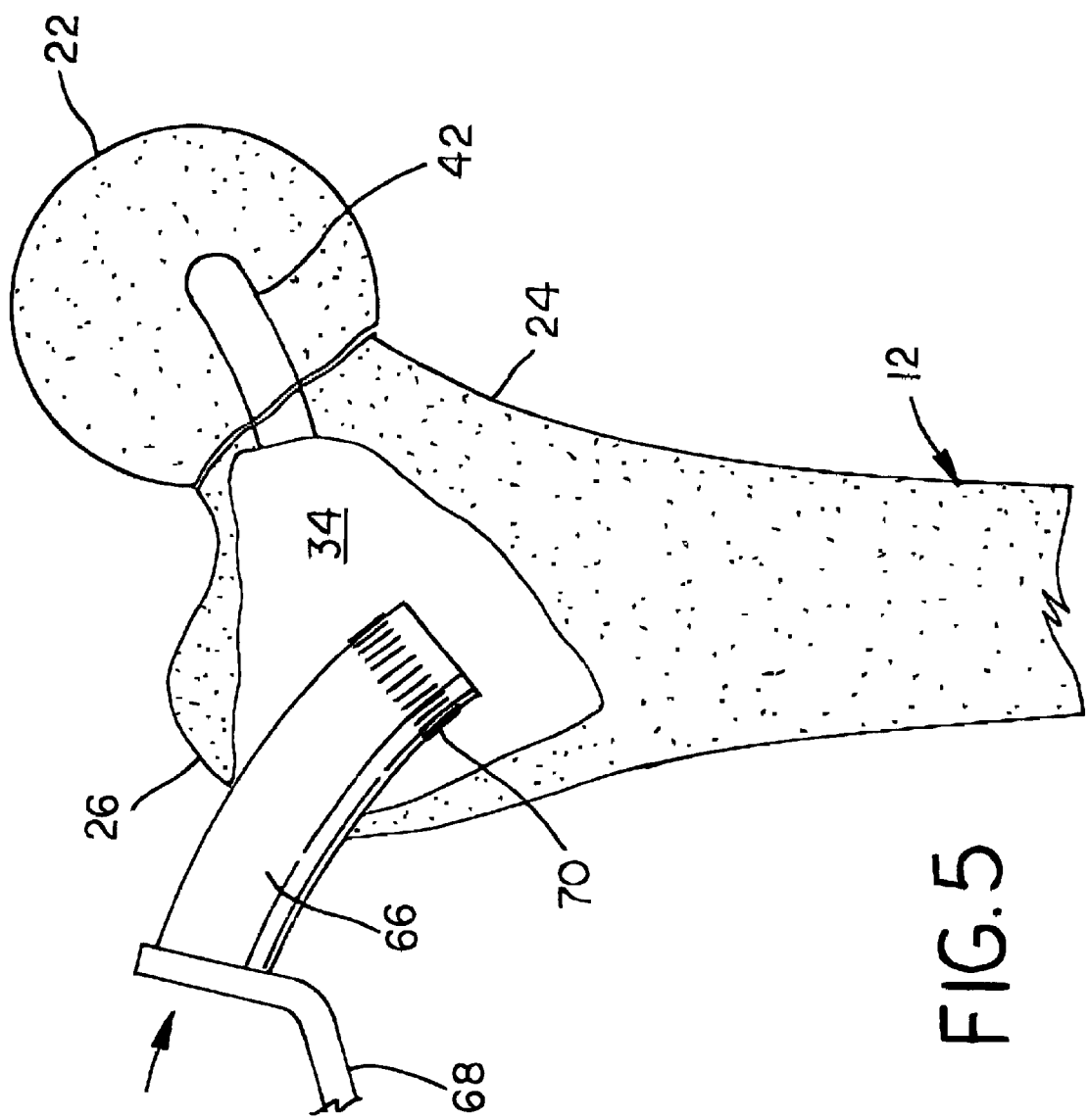
FIG. 5 illustrates another guide tube placed within the cavity in the femur.
Figure 6:
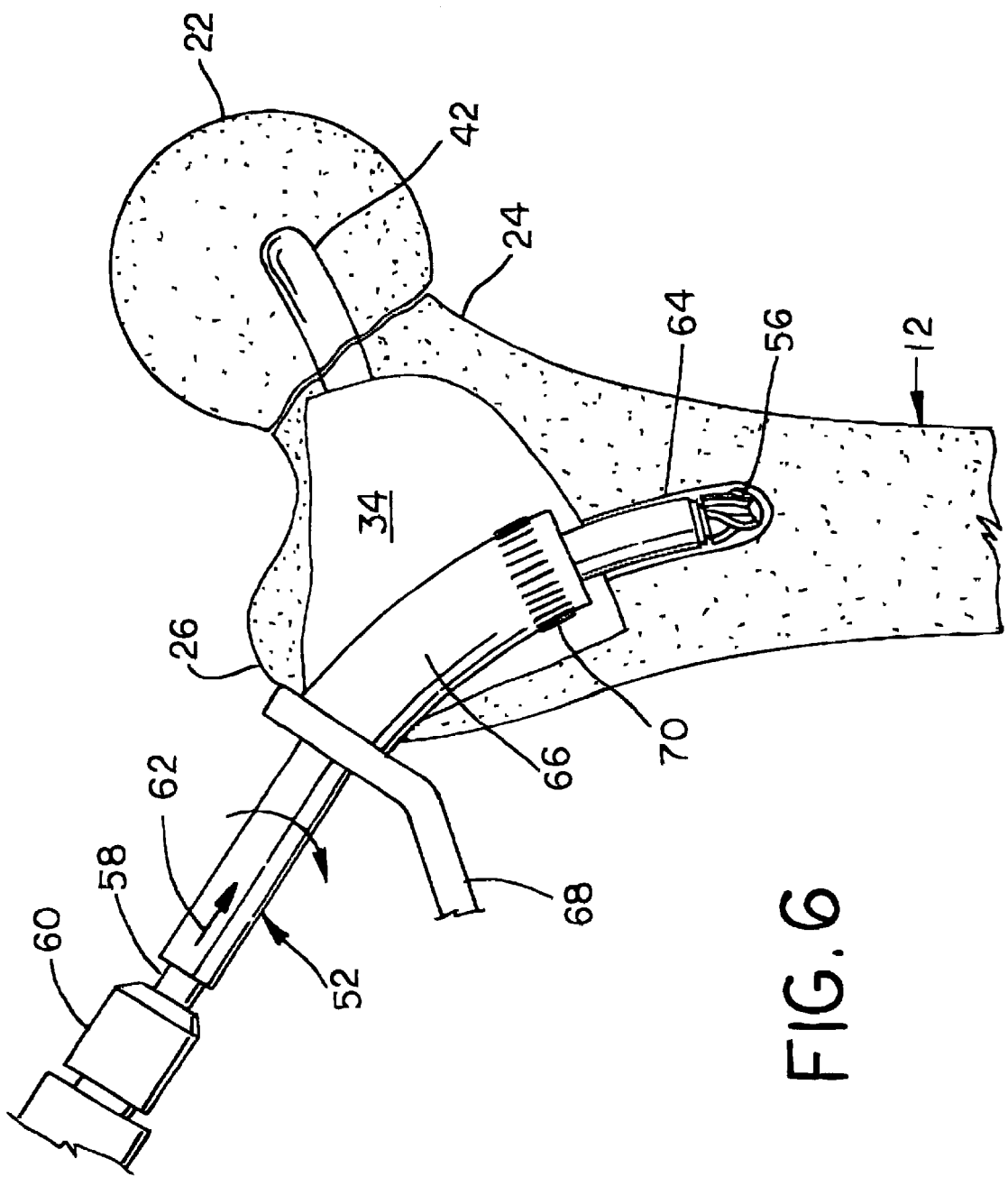
FIG. 6 illustrates the flexible reamer inserted through the curved guide tube of FIG. 6 to form an extension portion which extends into the shaft of the femur.

A second extension portion 64 of cavity 34 may also optionally be formed within femur 12 (FIGS. 5 and 6). Second extension portion 64 preferably extends into IM canal 38 within femur 12. To this end, a second hollow guide tube 66 is inserted within cavity 34. Guide tube 66 preferably also includes a handle 68 for locating and placement within cavity 34. Guide tube 66 has a curvature which is different from the curvature of guide tube 44, thus allowing second extension portion 64 to extend into IM canal 38 of femur 12. The exact curvature of guide tube 66 and guide tube 44 of course may vary from one application to another, or in fact may be the same under certain circumstances. In general, the curvature of a guide tube used to form first extension portion 42 is selected such that first extension portion 42 extends generally parallel to load axis 48 of femoral head 22, while another guide tube is selected such that second extension portion 64 extends into and preferably parallel with IM canal 38. Guide tube 66 may also include a knurled outer surface 70 which at least in some circumstances provides gripping engagement with interior walls of cavity 34. For example, if the diameter of knurled outer surface 70 is slightly larger than the diameter of drill bit 32, guide tube 66 may at least grip the interior walls of cavity 34 extending generally parallel to the drawings of FIGS. 5 and 6 at opposite sides of guide tube 66.

After placement of guide tube 66 within cavity 34 as shown in FIG. 6, flexible reamer 52 is used to form second extension portion 64 within femur 12. The depth of second extension portion 64 generally corresponds to the length of a bag 13 which is implanted within cavity 34, as will be described in more detail hereinafter.

In the embodiment shown in the drawings, a same flexible reamer 52 is used to form each of first extension portion 42 and second extension portion 64 of cavity 34. However, it is to be appreciated that a flexible reamer having a different diameter cutting head may be utilized if it is desirable to form first extension portion 42 and second extension portion 64 with different diameters.

Figure 7:
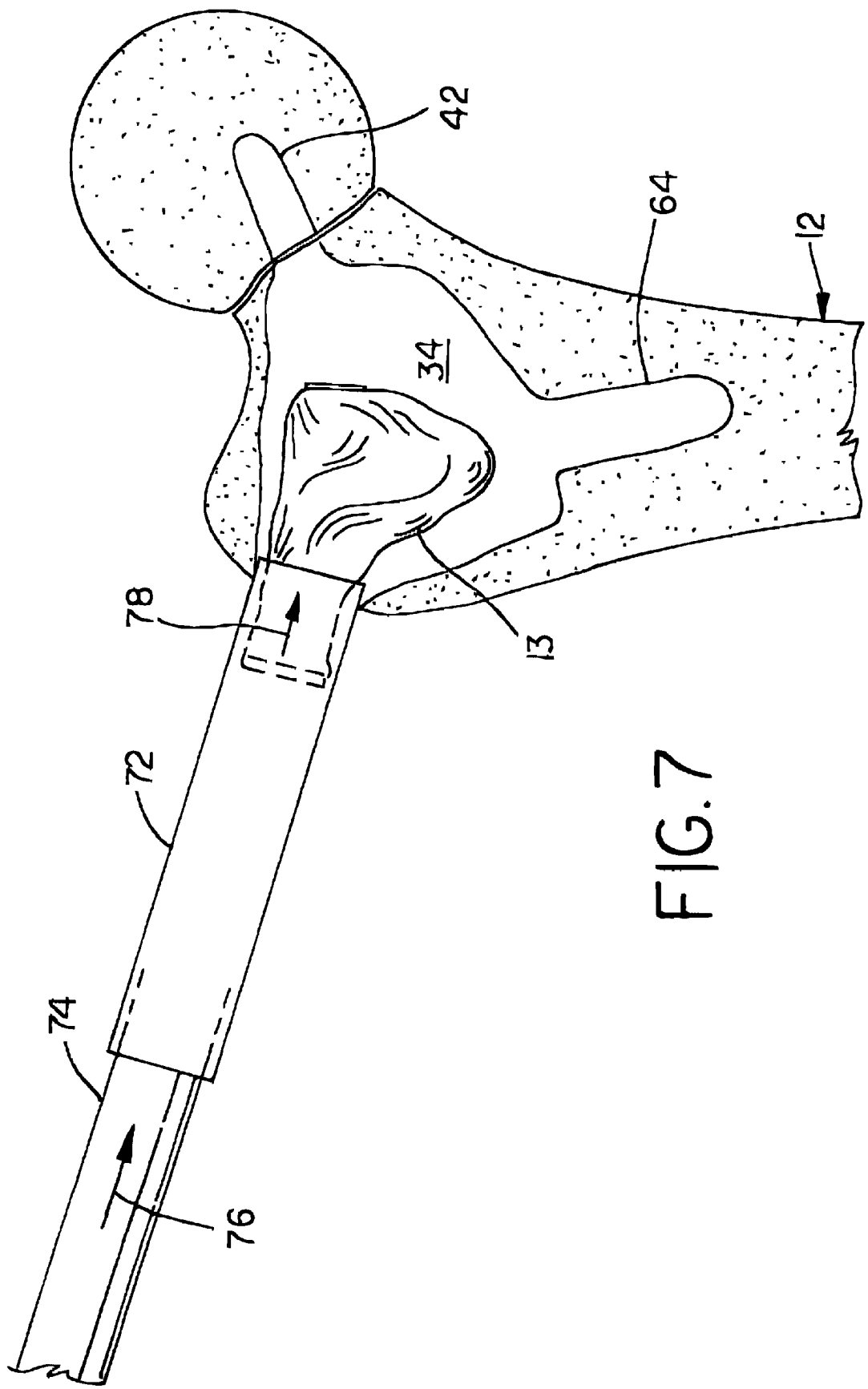
FIG. 7 illustrates a flexible bag being inserted within the cavity in the femur.
Figure 8:
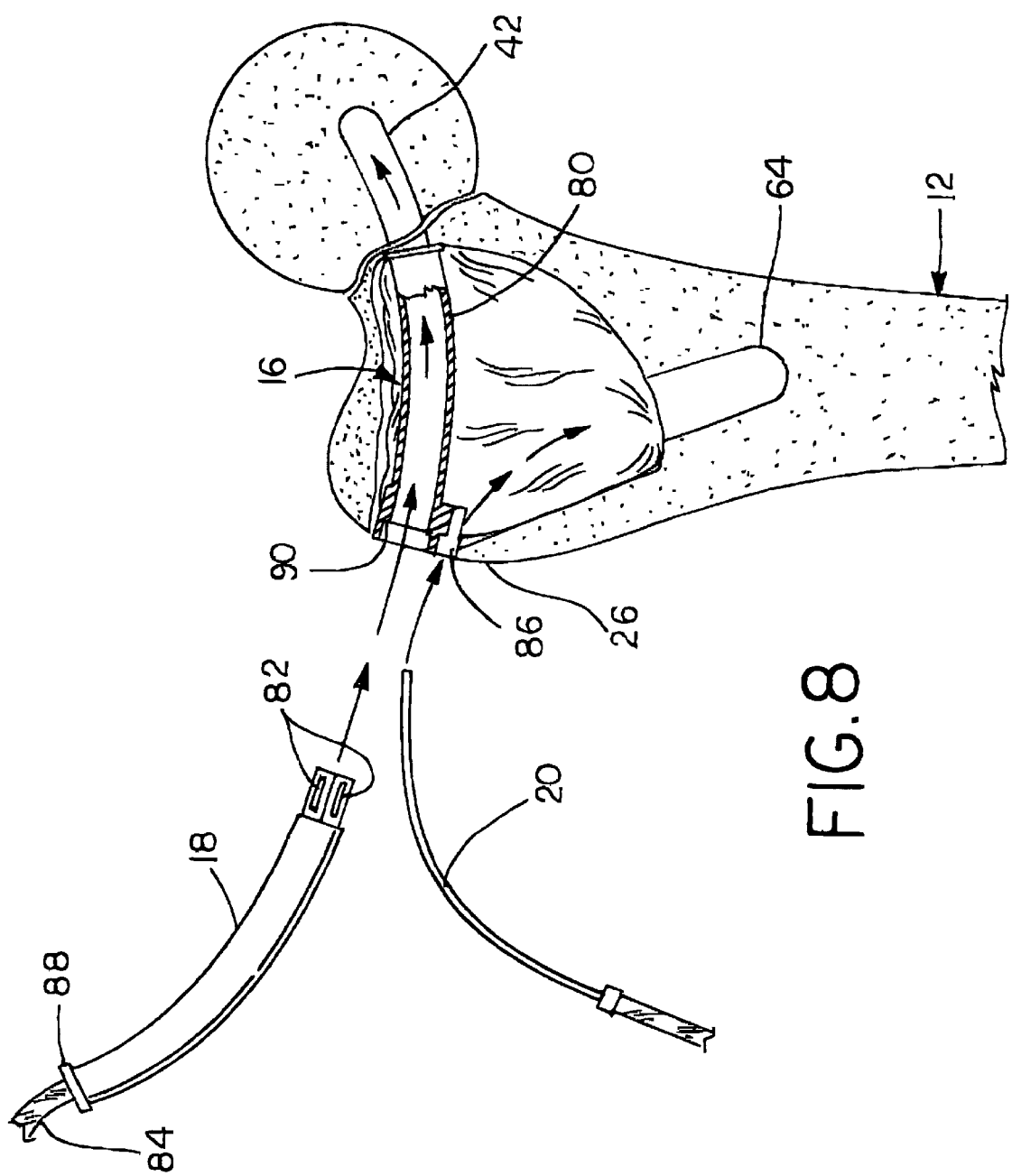
FIG. 8 illustrates the curved tube portion within the flexible bag, as well as the injection tubes which may be inserted within the flexible bag.

After formation of cavity 34 within femur 12, including first extension portion 42 and second extension portion 64, flexible bag 13 is inserted within cavity 34 (FIG. 7). Bag 13 may be folded in a suitable manner and inserted within a pre-load tube 72. Pre-load tube 72 has an outside diameter which is sized to fit within the entrance opening to cavity 34 within femur 12. A plunger 74 having an outside diameter which is slightly less than a inside diameter of pre-load tube 72 may be moved in an axial direction, indicated by arrow 76, to push bag 13 into cavity 34, as indicated by arrow 78. Bag 13 has a shape which generally corresponds to the shape of cavity 34, including first extension portion 42 and second extension portion 64. Alternatively, bag 13 may be formed from an elastomeric material allowing expansion under pressure into first extension portion 42 and second extension portion 64. Bag 13 is preferably formed from a porous material such that polymer 14 is allowed to seep therethrough at least to some extent into cancellous bone surrounding cavity 34.

Bag 13 (FIG. 8) includes structural support 16 with a curved tube portion 80 extending from an entrance of cavity 34 to an entrance of extension portion 42. Bag 13 may be suitably attached to curved tube portion 80, such as by using an adhesive, ultrasonic welding, etc. Curved tube portion 80 has an inside diameter allowing structural support 18 in the form of a hollow injection tube to be inserted therethrough. Injection tube 18 includes a plurality of apertures 82 at an end thereof through which the polymer may be injected. Hollow injection tube 18 and curved tube portion 80 are each formed from metal with complimentary curvatures, in the embodiment shown. A flexible hose 84 is connected to an end of injection tube 18 opposite from apertures 82, and receives pressurized high strength polymer from a pressure source such as a pump or the like (not shown). Structural support 16 also includes a distal opening 86 adjacent greater trochanter 26 of femur 12 allowing structural support 20 in the form of a second hollow injection tube to be inserted therethrough and into bag 13.

Hollow injection tube 18 is inserted into curved tube portion 80, and an end of injection tube 18 is positioned within femoral head 22 such that apertures 82 are near the end of first extension portion 42. The high strength polymer is then injected through hose 84 and injection tube 18 to apertures 82. The polymer may be polymethylmethacrylate (PMMA). The polymer is preferably a curable polymer, such as with thermal energy, light energy, X-ray energy or a chemical catalyst.

Figure 9:
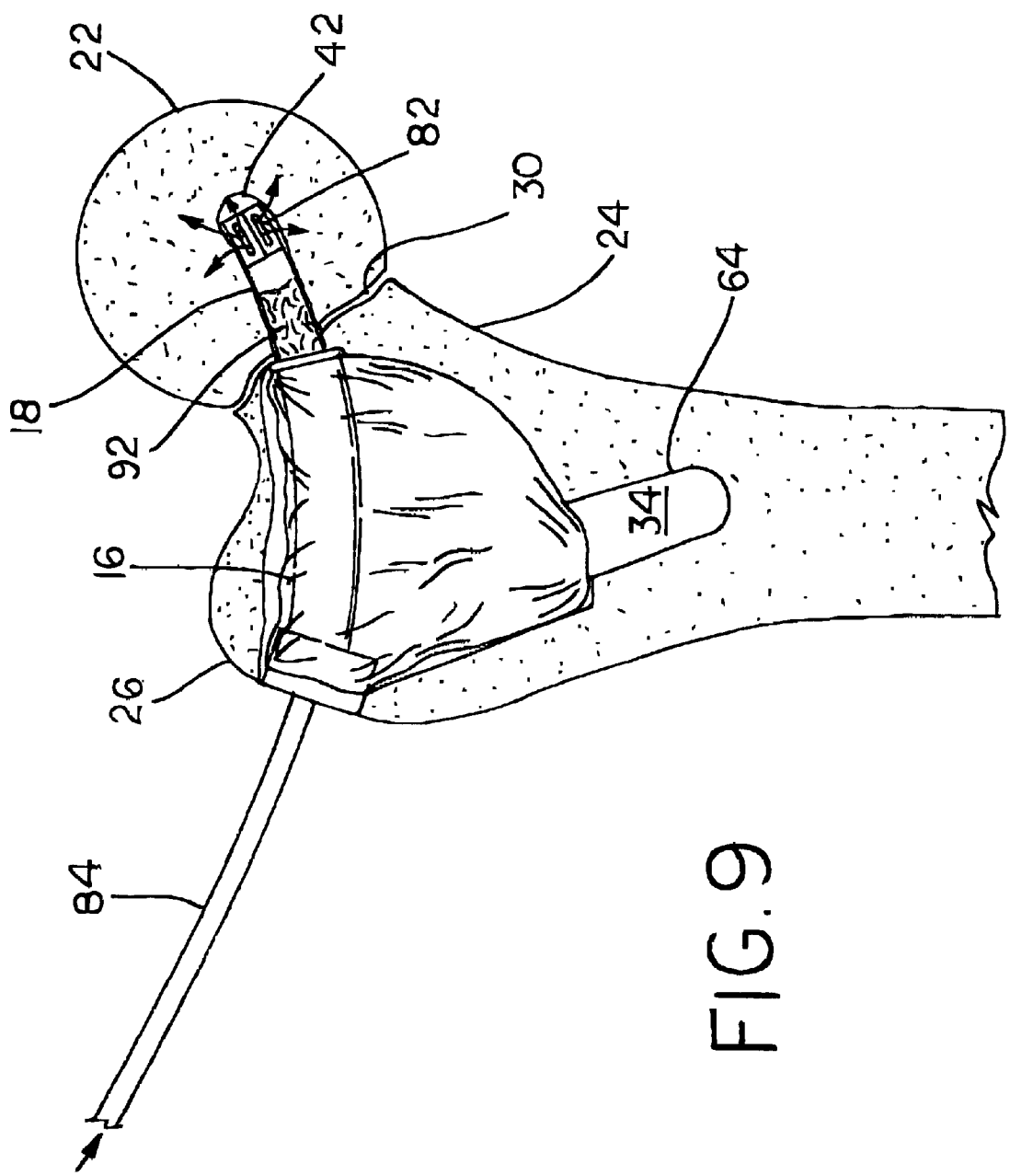
FIG. 9 illustrates injection of the high strength polymer within the femoral head using an injection tube shown in FIG. 8.
Figure 10:
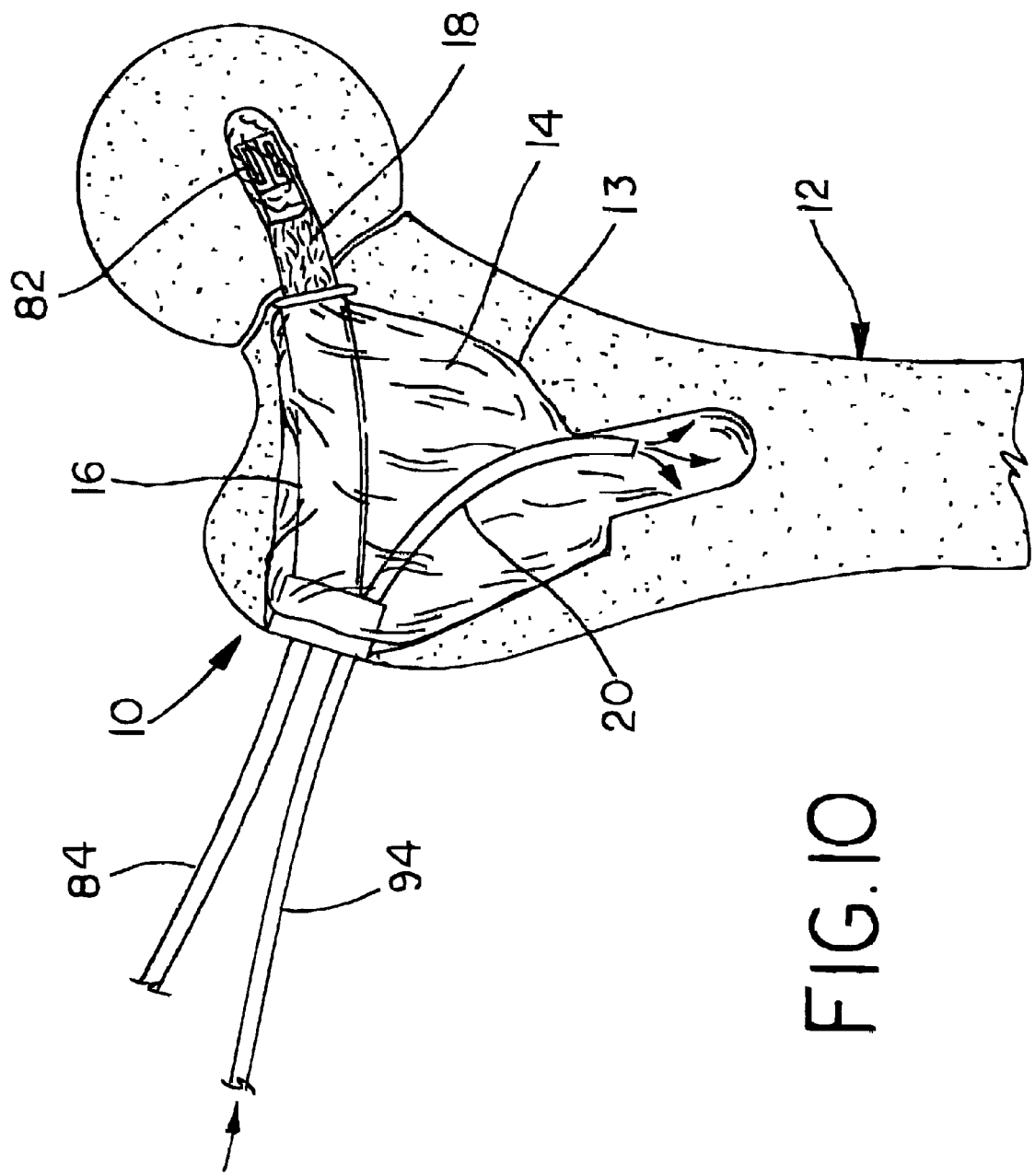
FIG. 10 illustrates injection of a high strength polymer within a distal portion of the bag using another injection tube shown in FIG. 8.
Figure 11:
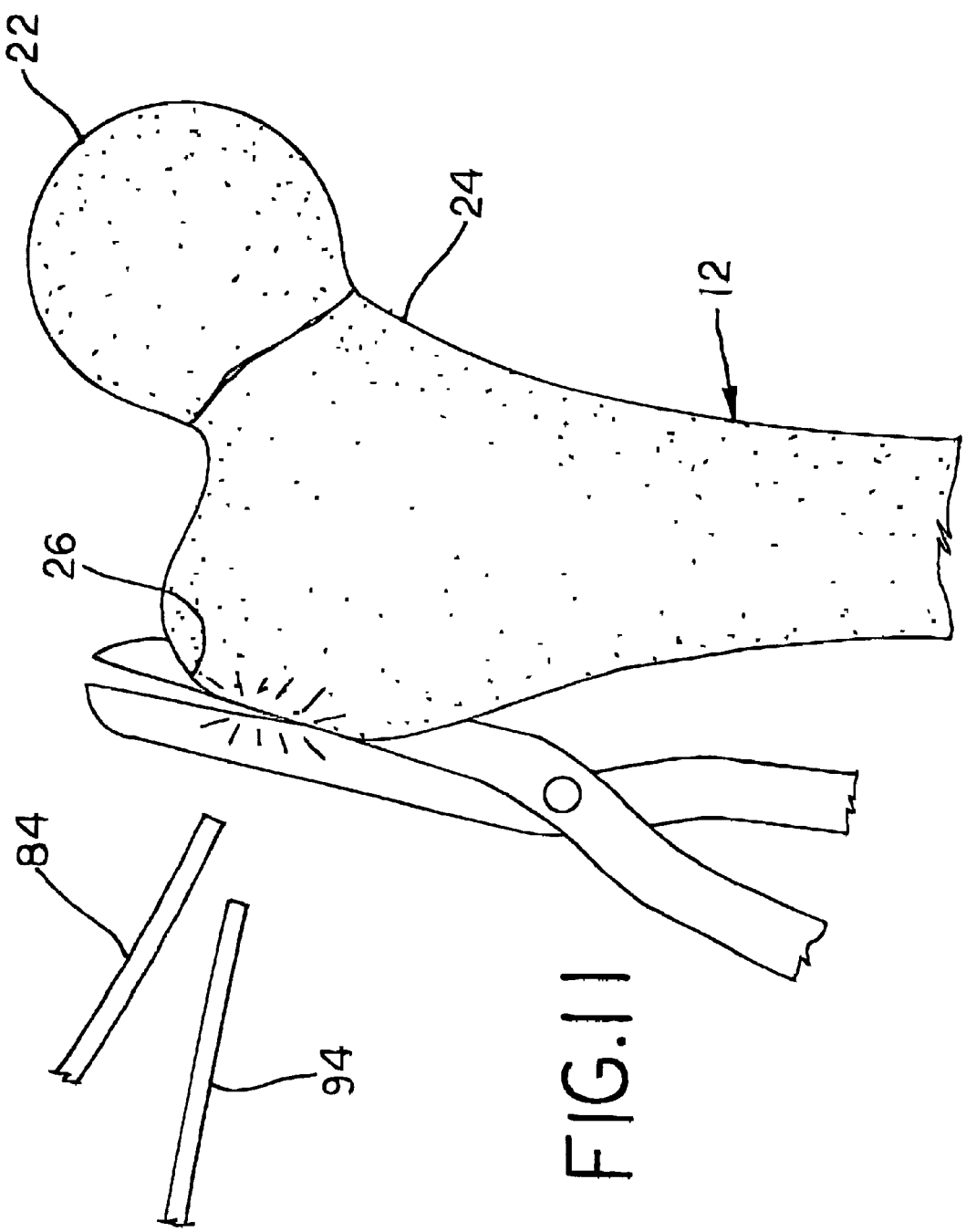
FIG. 11 illustrates the flexible fill hoses being snipped from the implant within the femur.

To allow loading between femoral head 22 and neck 24, injection tube 18 is structured and arranged to be slidably disposed within curved tube portion 16 after implanting within femur 12. More particularly, injection tube 18 may include a sealant 92 such as a resorbable sealant surrounding a portion thereof adjacent the inside diameter of curved tube portion 16 (FIG. 9). For example, the sealant may be in the form of glycerin which surrounds injection tube 18. The glycerin is resorbed over time after implanting of orthopaedic implant 10 within femur 12. A small clearance distance thus exists between injection tube 18 and curved tube portion 16 after resorption of the glycerin. In this manner, injection tube 18 is slidably movable within curved tube portion 16.

Figure 12:
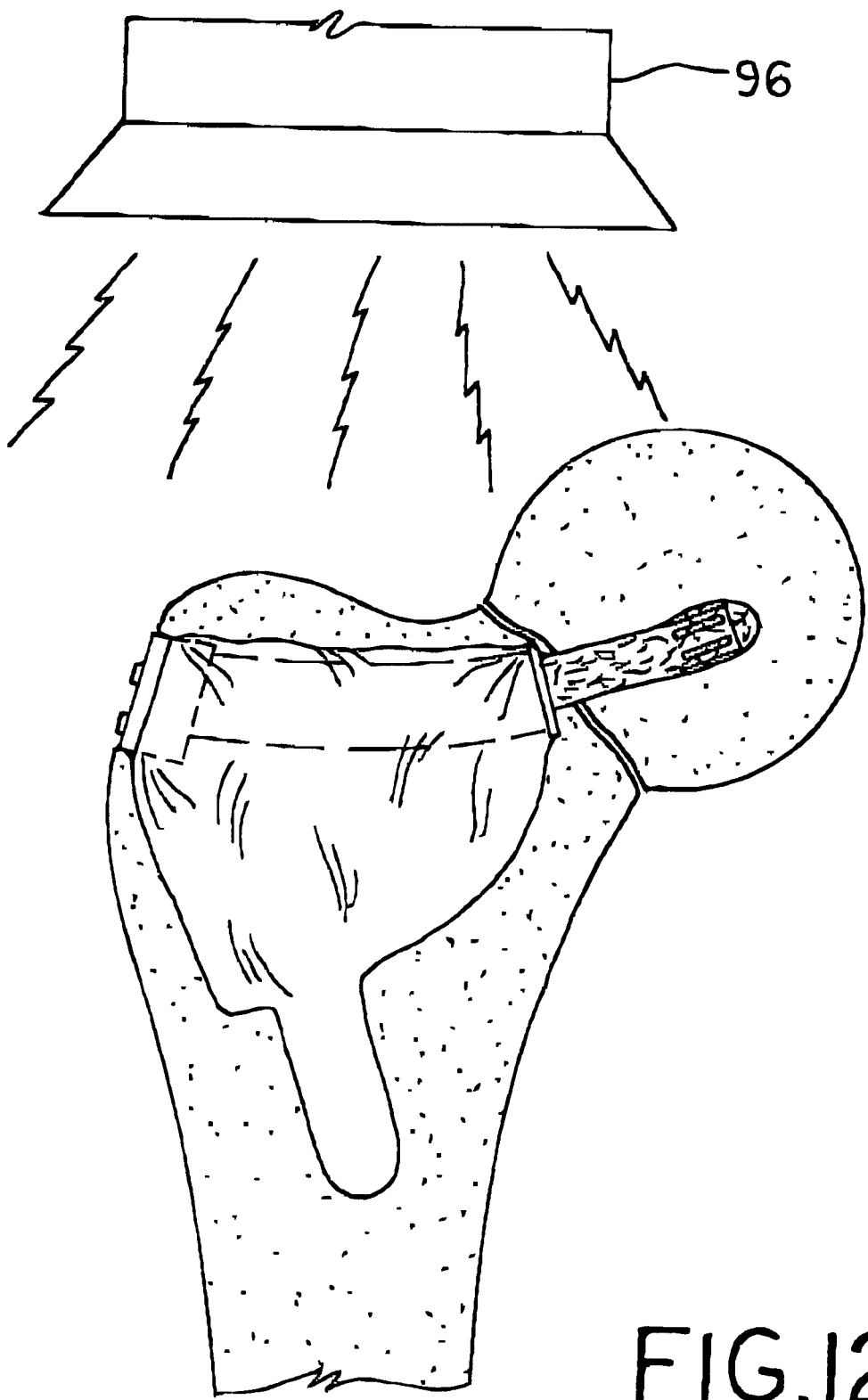
FIG. 12 illustrates one technique for curing the polymer within the flexible bag.
Figure 13:
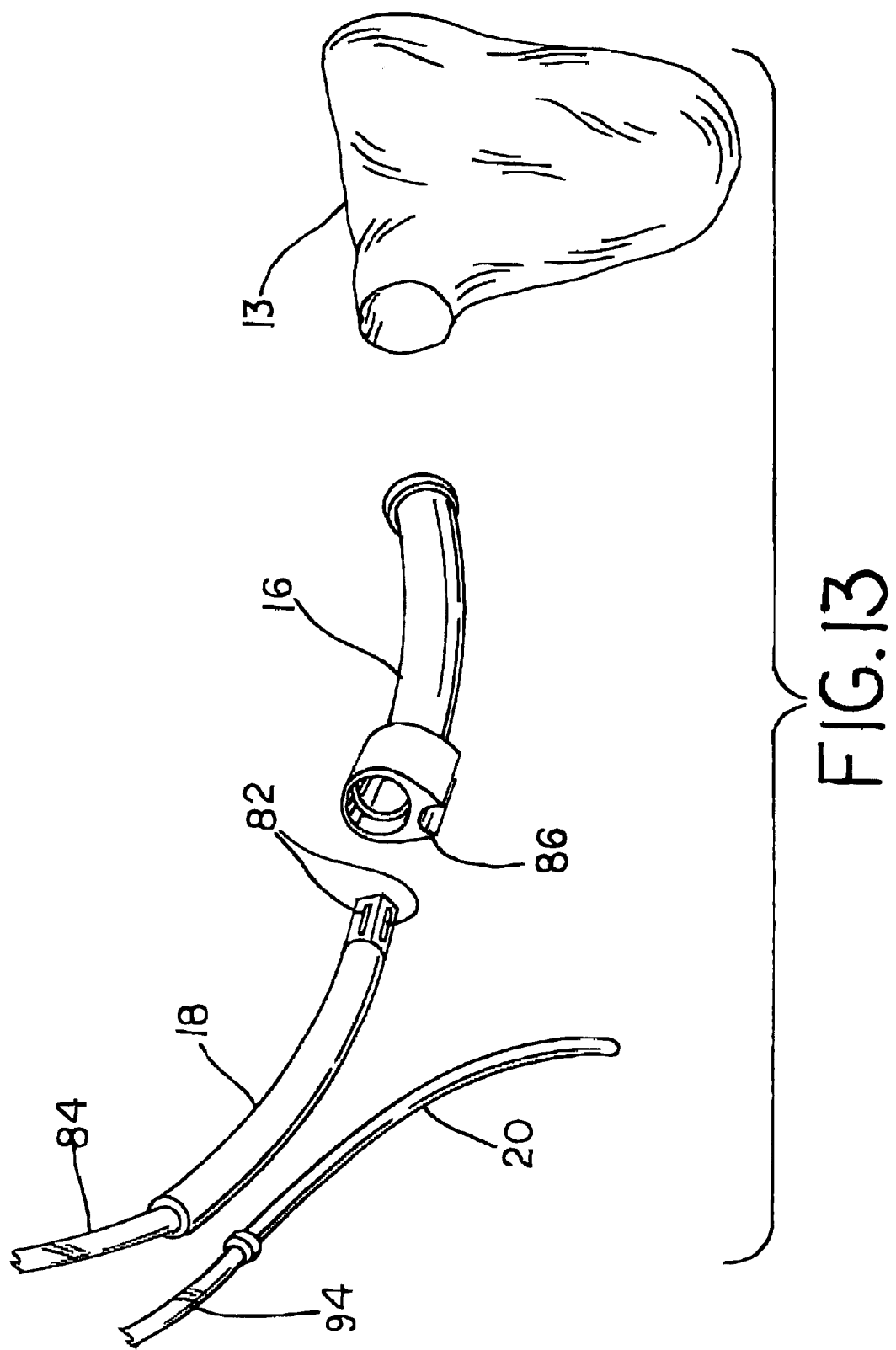
FIG. 13 is an exploded view of the porous, flexible bag and injection tubes.

Injection tube 20 is slid through distal opening 86 of structural support 16 within bag 13. Injection tube 20 is selected with a curvature which preferably extends into second extension portion 64. A polymer is injected under pressure within bag 13 such that bag 13 extends into and substantially fills second extension portion 64 of cavity 34. Bag 13 can either be contoured to fit within second extension portion 64, or may be contourable (e.g., expandable) to fit within second extension portion 64. The polymer may be a same type of polymer as is injected into first extension portion 42 within femoral head 22, or may be different. In the embodiment shown in FIGS. 9 and 10, the polymer includes a chemical catalyst prior to injection which causes the polymer to cure. Flexible hoses 84 and 94 may thus be cut from injection tubes 18 and 20, which remain within orthopaedic implant 10. Alternatively, the polymer within bag 13 may be cured with another source of energy, such as X-ray energy emitted from an X-ray source 96 (FIG. 12).

Figure 14:
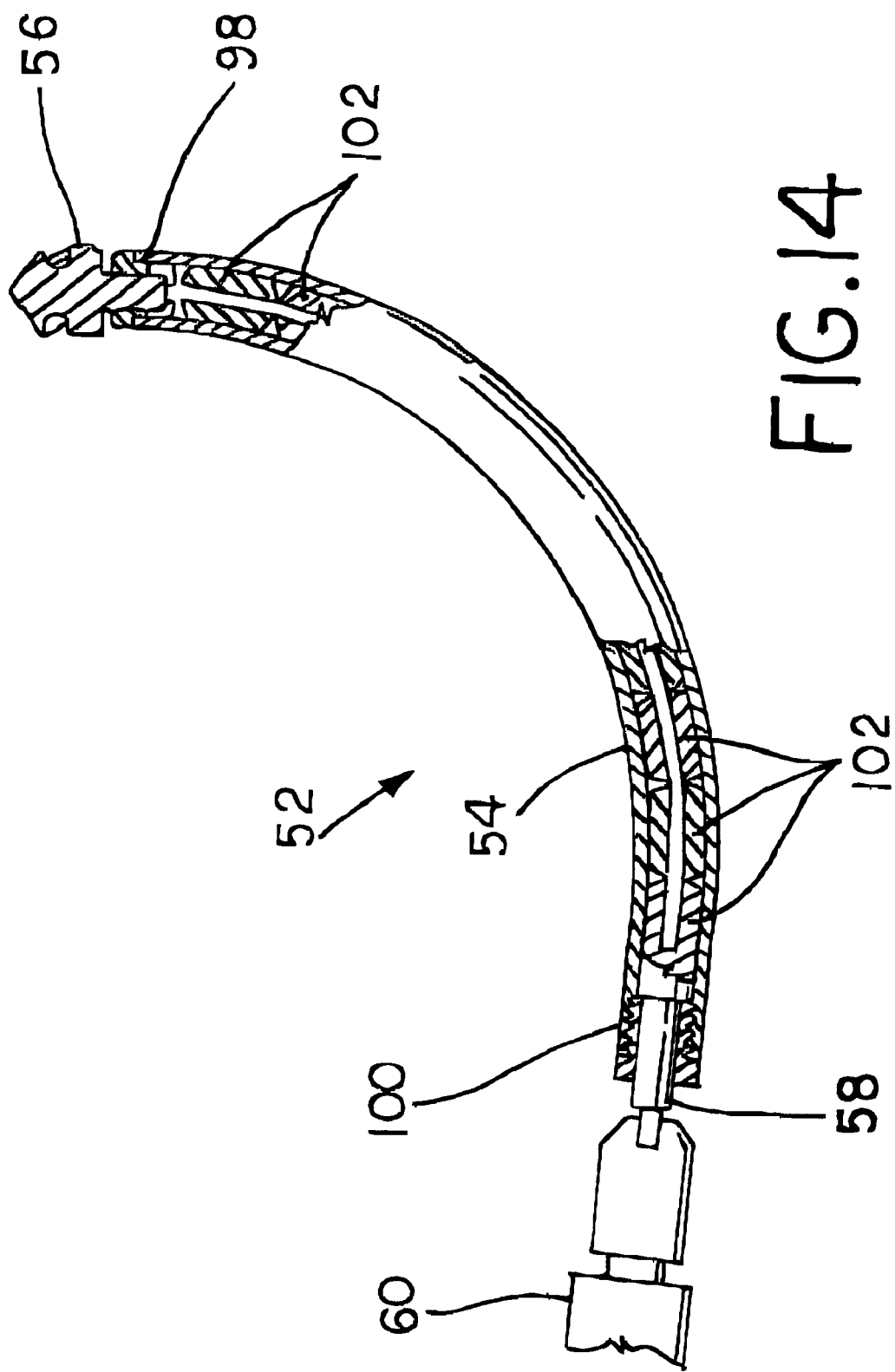
FIG. 14 is a side, partially fragmentary view of the flexible reamer shown in FIGS. 4 and 6.
Figure 15:
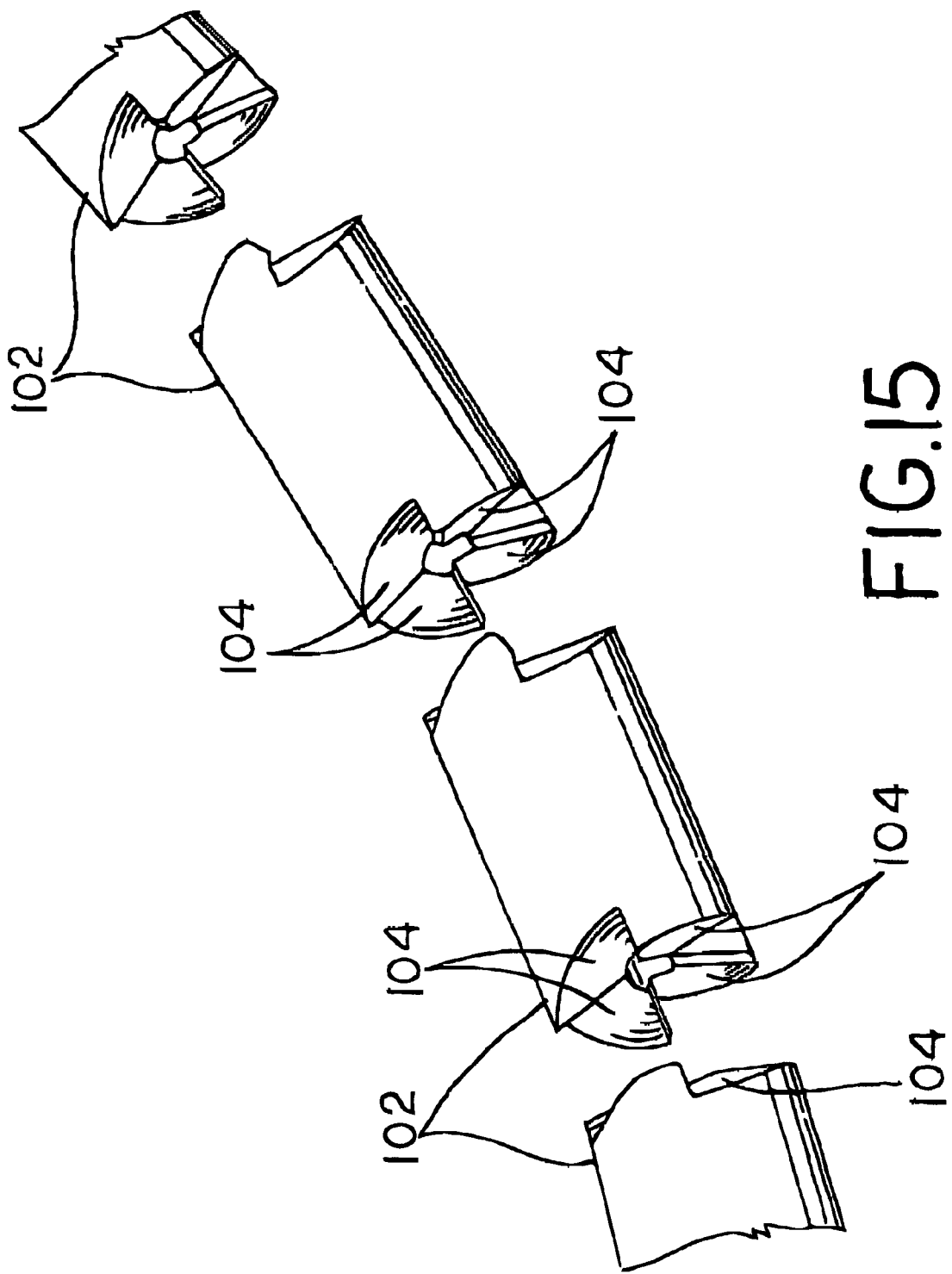
FIG. 15 is a perspective view of a number of the drive gears located within the hollow tube of the flexible reamer shown in FIG. 14.

Referring now to FIGS. 14 and 15, flexible reamer 52 is shown in greater detail. Cutting head 56 is carried by and extends from an end 98 of hollow tube 54. Driven shank 58 is carried by and extends from an opposite end 100 of flexible tube 54. A plurality of drive gears 102 are rotatably disposed within flexible tube 54. Drive gears 102 engage each other in an end-to-end manner and interconnect driven shank 58 with cutting head 56. Thus, rotation of driven shank 58 using drive source 60 in turn causes rotation of cutting head 56. Each drive gear 102 includes four axially facing gear teeth 104 at each end thereof. Gear teeth 104 are angled to allow flexible hollow tube 54 to bend, while still ensuring positive driving engagement between adjacent drive gears 102 within tube 54.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic implant, comprising:
   a flexible bag;
   a structural support at least partially within said bag;
   said structural support comprising a hollow injection tube for injecting said polymer; and
   a hardenable polymer within said bag.

2. The orthopaedic implant of claim 1, wherein said hollow injection tube is comprised of metal.

3. The orthopaedic implant of claim 1, wherein said structural support extends from said bag.

4. The orthopaedic implant of claim 1, wherein said bag is expandable under pressure.

5. The orthopaedic implant of claim 1, wherein said bag comprises a porous bag allowing some of said polymer to pass therethrough.

6. The orthopaedic implant of claim 1, wherein said polymer comprises a curable polymer.

7. The orthopaedic implant of claim 6, wherein said polymer is curable with one of thermal energy, light energy, X-ray energy and a chemical catalyst.

8. The orthopaedic implant of claim 6, wherein said polymer comprises a bioresorbable polymer.

9. The orthopaedic implant of claim 6, wherein said polymer comprises polymethylmethacrylate.

* * * * *